United States Patent [19]
Andoh et al.

[11] Patent Number: 5,030,455
[45] Date of Patent: Jul. 9, 1991

[54] SUSTAINED-RELEASE DRUG PREPARATION

[75] Inventors: Hidenobu Andoh, Gifu; Sumio Watanabe; Yasuo Miyake, both of Aichi, all of Japan

[73] Assignee: Eisai Co., Ltd., Tokyo, Japan

[21] Appl. No.: 396,838

[22] Filed: Aug. 22, 1989

Related U.S. Application Data

[63] Continuation-in-part of Ser. No. 73,827, Jul. 15, 1987, abandoned.

[30] Foreign Application Priority Data

Jul. 18, 1986 [JP] Japan ................. 61-167865

[51] Int. Cl.⁵ .............................................. A61K 9/26

[52] U.S. Cl. .................................. 424/468; 424/469; 424/470

[58] Field of Search ................ 424/465, 468, 469, 470

[56] References Cited

U.S. PATENT DOCUMENTS

| | | | |
|---|---|---|---|
| 2,895,881 | 7/1959 | Hamada | 424/468 X |
| 3,459,850 | 8/1969 | Riva | 424/468 OR |
| 4,163,777 | 8/1979 | Mitra | 424/468 OR |
| 4,375,468 | 3/1983 | Dunn | 424/468 X |

*Primary Examiner*—Karl Group
*Attorney, Agent, or Firm*—Wenderoth, Lind & Ponack

[57] ABSTRACT

A sustained-release drug preparation comprises a water-soluble drug, a lipidic substance and an oil as its essential components. The drug level in the blood is sustained at a preferable concentration for a long period of time.

5 Claims, 5 Drawing Sheets

SUSTAINED-RELEASE DRUG PREPARATION

This application is a continuation-in-part of Ser. No. 073,827, filed on July 15, 1987, now abandoned.

BACKGROUND OF THE INVENTION

1.) Field of the Invention

This invention relates to a drug preparation which comprises a water-soluble drug, a lipidic substance and an oil as essential components and is suitable for oral administration. When the drug preparation of this invention is administered orally, the velocity of dissolving out the drug in the body is controlled as desired so that the drug level in the blood is maintained at a preferable concentration for a long period of time. The drug preparation of this invention is therefore useful as a pharmaceutical product.

2.) Description of the Prior Art

As means for controlling the duration time of a drug administered orally for therapeutic purposes, various methods have already been proposed including, for example, (i) to disperse a drug in a base insoluble in water such as fat or wax by either dissolving or melting the drug in the base, (ii) to enclose a drug in a physiologically-inert plastic base so that upon its administration, the plastic base remains undigested in the body and is eventually discharged out of the body, and (iii) to disperse a drugs in a hydrophilic high-molecular substance so that upon administration, the high-molecular substance is gelled and the drug is gradually dissolved and released from the resultant viscous layer of the thus-gelled high-molecular substance.

Following the above-described conventional techniques, the present inventors conducted a detailed test on the dissolution of effective drug. As a result, the present inventors felt the desire for the provision of a technique which allows to control the velocity of dissolution of a drug as desired by a simple method.

SUMMARY OF THE INVENTION

Based on the above-mentioned finding, the present inventors have carried out an extensive investigation.

As a result of the above investigation, it has been found that the velocity of dissolution of a drug can be controlled by using an oil and a lipidic substance in combination.

In one aspect of this invention, there is thus provided a sustained-release drug preparation comprising as essential components a water-soluble drug, a lipidic substance and an oil.

The sustained-release drug preparation is free of the aforementioned problems of the prior art, namely, has solved the difficulties in the conventional sustained-release means.

BRIEF DESCRIPTION OF THE DRAWINGS

The above and other objects, features and advantages of this invention will become apparent from the following description of the invention and the appended claims, taken in conjuction with the accompanying drawings, in which:

DETAILED DESCRIPTION OF THE INVENTION AND PREFERRED EMBODIMENTS

Figure 1:
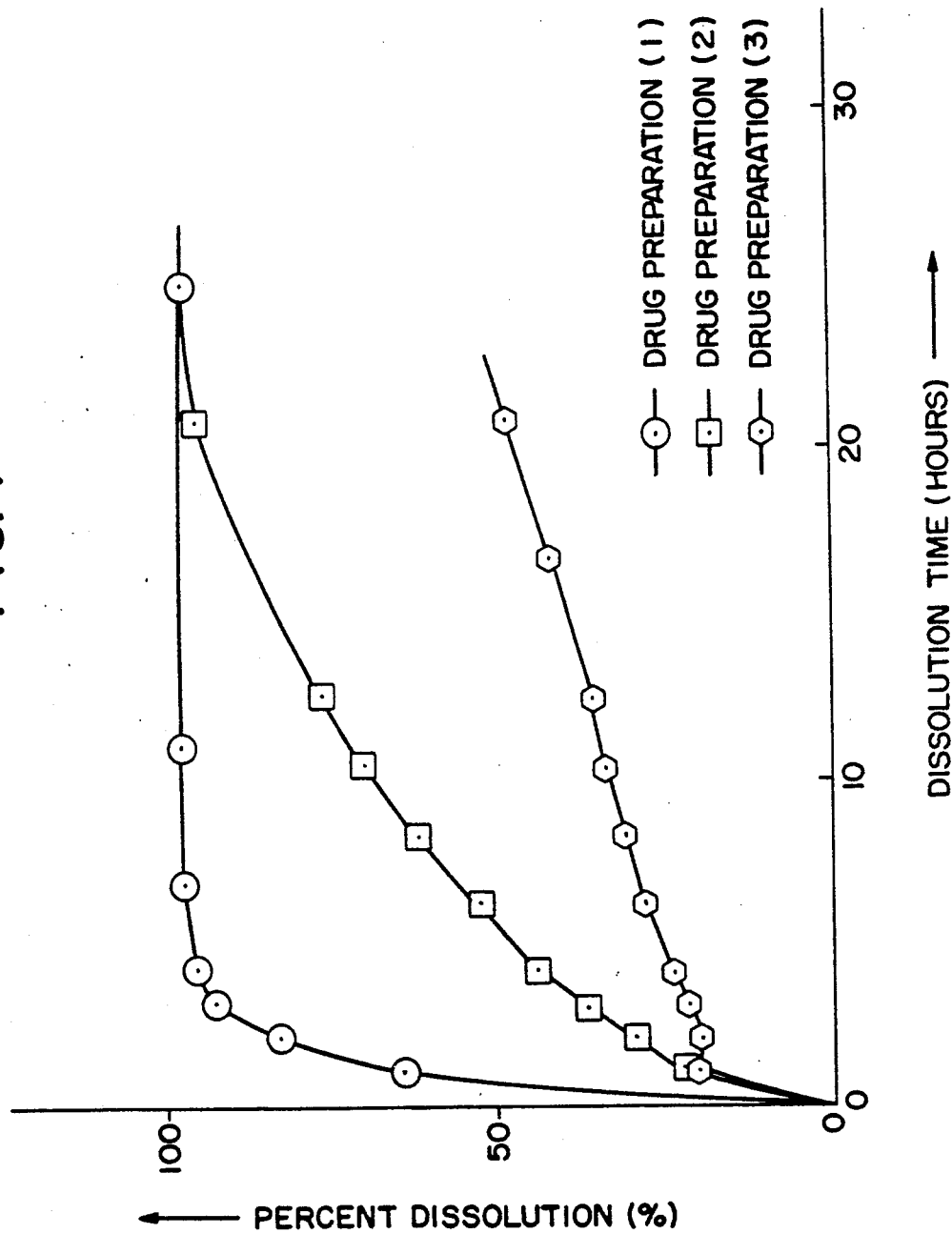
FIGS. 1-5 diagrammatically and respectively illustrate the velocities of dissolution of drugs from their drug preparations of this invention in comparison with those of the same drugs from corresponding controls.

The oral drug in the novel drug preparation of this invention is a water-soluble drug. As its illustrative examples, may be mentioned bunazosin hydrochloride, phenylpropanolamine, chlorphenylamine maleate and theophylline, and the like.

As exemplary lipidic substances suitable for the formulation of the drug preparation of this invention are those which are normally solid or semi-solid at ambient (room) temperature and among these, may be mentioned aliphatic higher fatty acids such as stearic acid, myristic acid and palmitic acid, and aliphatic higher alcohols such as lauryl alcohol, myristyl alcohol and stearyl alcohol; in addition, esters of higher fatty acids such as the monostearate, distearate and tristearate of glycerin and hydrogenated castor oil, waxes such as bees wax, carnauba wax, Japan wax and whale wax, and hydrocarbons such as paraffin, microcrystalline wax and ceresine; and especially the sucrose esters of fatty acids. They may be used either singly or in combination.

Illustrative of the oil usable in the present invention are those which are normally liquid at ambient (room) temperature and they may include soybean oil, cotton seed oil, sesame oil, peanut oil, olive oil, sufflower oil, octyldodecyl glyceride, migriol, glycerin monocaprylate, silicone oil, etc. They may be used either singly or in combination.

In addition to the above-described three essential components, the drug preparation of this invention may also contain, in suitable amount or amounts, one of more desired adjuvants such as those to be described below.

Lactose, crystalline cellulose ("Avicel for Drug and Food Applications", trade name), corn starch, mannitol, talc, silicic acid, calcium stearate, shellac, polyvinyl pyrrolidone, hydroxypropylcellulose, ethylcellulose, calcium carboxymethylcellulose, sodium carboxymethylcellulose, carboxymethylcellulose, hydroxypropylmethylcellulose, etc.

The drug preparation of this invention is obtained by mixing the above-mentioned components at a suitable ratio and then forming the resultant mixture into a preparation form suitable for oral administration such as granules, powder capsules, granule capsules or compression-formed tablets.

As will be shown subsequently by experimental results, the velocity of dissolution of the pharmaceutically-effective component, i.e., the drug from the drug preparation of this invention can be controlled so that its dissolution lasts for many hours.

The drug preparation of this invention will hereinafter be described specifically by the following Examples.

EXAMPLE 1

By using components of Table 1 in their respective amounts shown in the same table, three kinds of drug preparations (1), (2) and (3) were separately formulated in the following manner.

In accordance with each of the formulations of the drug preparations (1), (2) and (3) shown in Table 1, bunazosin hydrochloride, "S-370" (trade name, the sucrose ester of a fatty acid) and "Ethocel-10" (trade name) were mixed for 3 minutes in a 20-l super mixer. Then, ethanol was added solely or both octyldodecyl glyceride and ethanol were added in combination. The resultant mixture was kneaded for 3 minutes. The thus-prepared three kinds of masses were separately granulated in a cylindrical granulator equipped with a screen whose openings had a diameter of 0.5 mm. After drying them in a tray dryer, they were separately sifted to 16–60 mesh so as to provide the drug preparations (1), (2) and (3).

TABLE 1

| Component mixed | Drug preparation | | |
|---|---|---|---|
| | (1) (g) | (2) (g) | (3) (g) |
| Bunazosin hydrochloride | 100 | 100 | 100 |
| Sucrose ester of fatty acid (S-370) | 800 | 700 | 600 |
| Ethocel-10 (adjuvant) (ethylcellulose) | 100 | 100 | 100 |
| Octyldodecyl glyceride | — | 100 | 200 |
| Total | 1000 | 1000 | 1000 |

EXAMPLE 2

By using components of Table 2 in their respective amounts shown in the same table, two kinds of drug preparations (4) and (5) were separately formulated following the procedure of Example 1 except that the mixing and kneading operations in the super mixer and the granulating operation were each carried out in a state heated at 60°–70° C.

In the above-described manner, the preparations (4) and (5) were obtained in granular forms.

TABLE 2

| Component mixed | Drug preparation | |
|---|---|---|
| | (4) (g) | (5) (g) |
| Bunazosin hydrochloride | 200 | 200 |
| Stearic acid | 800 | 750 |
| Sesame oil | — | 50 |
| Total | 1000 | 1000 |

EXAMPLE 3

Following the procedure of Example 2, a granular drug preparations (6) and (7) of compositions shown respectively in Table 3 were formulated.

TABLE 3

| Component mixed | Drug preparation | |
|---|---|---|
| | (6) (g) | (7) (g) |
| Theophylline | 400 | 400 |
| Stearic monoglyceride | 600 | 550 |
| Migriol | — | 50 |
| Total | 1000 | 1000 |

EXAMPLE 4

Following the procedure of Example 2, a granular drug preparation (8) of a composition shown in Table 4 was formulated.

TABLE 4

| Component mixed | Drug preparation (8) (g) |
|---|---|
| Theophylline | 500 |
| Lovely wax (hardened castor oil) | 300 |
| Polyvinyl pyrrolidone (K-30) | 50 |
| Octyldodecyl glyceride | 150 |

TABLE 4-continued

| Component mixed | Drug preparation (8) (g) |
|---|---|
| Total | 1000 |

EXAMPLE 5

Following the procedure of Example 1, a granular drug preparation (9) of a composition shown in Table 5 was formulated.

TABLE 5

| Component mixed | Drug preparation (9) (g) |
|---|---|
| Chlorphenylamine maleate | 200 |
| Sucrose ester of fatty acid (S-370) | 500 |
| Ethocel-10 | 50 |
| Silicone oil | 200 |
| Total | 950 |

EXAMPLE 6

Following the procedure of Example 2, a granular drug preparation (10) of a composition shown in Table 6 was formulated.

TABLE 6

| Component mixed | Drug preparation (10) (g) |
|---|---|
| Phenylpropanolamine | 30 |
| Stearyl alcohol | 55 |
| Polyvinyl pyrrolidone (K-30) | 5 |
| Peanut oil | 10 |
| Total | 100 |

The degrees of controlled dissolution of the respective drugs from the corresponding granular drug preparations (1)–(9) were observed in the following manner in accordance with the puddle method. From the respective drug preparations, 100-mg portions were individually collected as samples. Using the second solution of the Japan Pharmacopoeia as a dissolving medium, each of the samples was subjected to dissolution. Their dissolved amounts were determined by comparing their u.v. (λ=245 nm) absorption data with standard calibration curves which had been prepared from u.v. absorption data obtained by measuring their corresponding drug solutions of prescribed known concentrations, for example, a bunazosin hydrochloride solution (standard solution) prepared separately in advance. The velocities of dissolution from the respective samples, in other words, their dissolution rates along the passage of time, which were obtained in the above-described manner, are shown in FIGS. 1–5.

Namely, FIGS. 1–5 diagrammatically show, as a function of time (hours), the rates of dissolution of the drugs from the corresponding drug preparations of this invention into the second solution prescribed in the Japan Pharmacopoeia along with the corresponding data of the samples of the control drug preparations (1), (4) and (6). In each of the drawings, the time of dissolution of the drug is plotted in hours along the axis of absissas while the percent dissolution is plotted in % along the axis of ordinates. In these drawings, the drug preparation (1) is a control as apparent from Table 1 of Example 1 and did not contain the oil component (octyldodecyl glyceride) among the three essential components in the present invention.

As readily envisaged from FIG. 1, the percent dissolution reached substantially 100% upon an elapsed time as early as 4 hours in the course of the measurement in the case of the control [the drug preparation (1)]. In contrast, the percent dissolution of the drug preparation (2) finally reached 100% after the lapse of 20 hours of the measurement time. In the case of the drug preparation (3), the percent dissolution was still as little as about 50% even after the lapse of 20 hours of the measurement time.

In addition, it is worthy to note that the drug preparations (2) and (3) have different dissolution curves (i.e., different inclinations) due to the difference in composition in spite of the use of the same components. As suggested by the curves, it is possible to control the velocity of dissolution of a drug as desired by changing the mixing ratio suitably.

Figure 2:
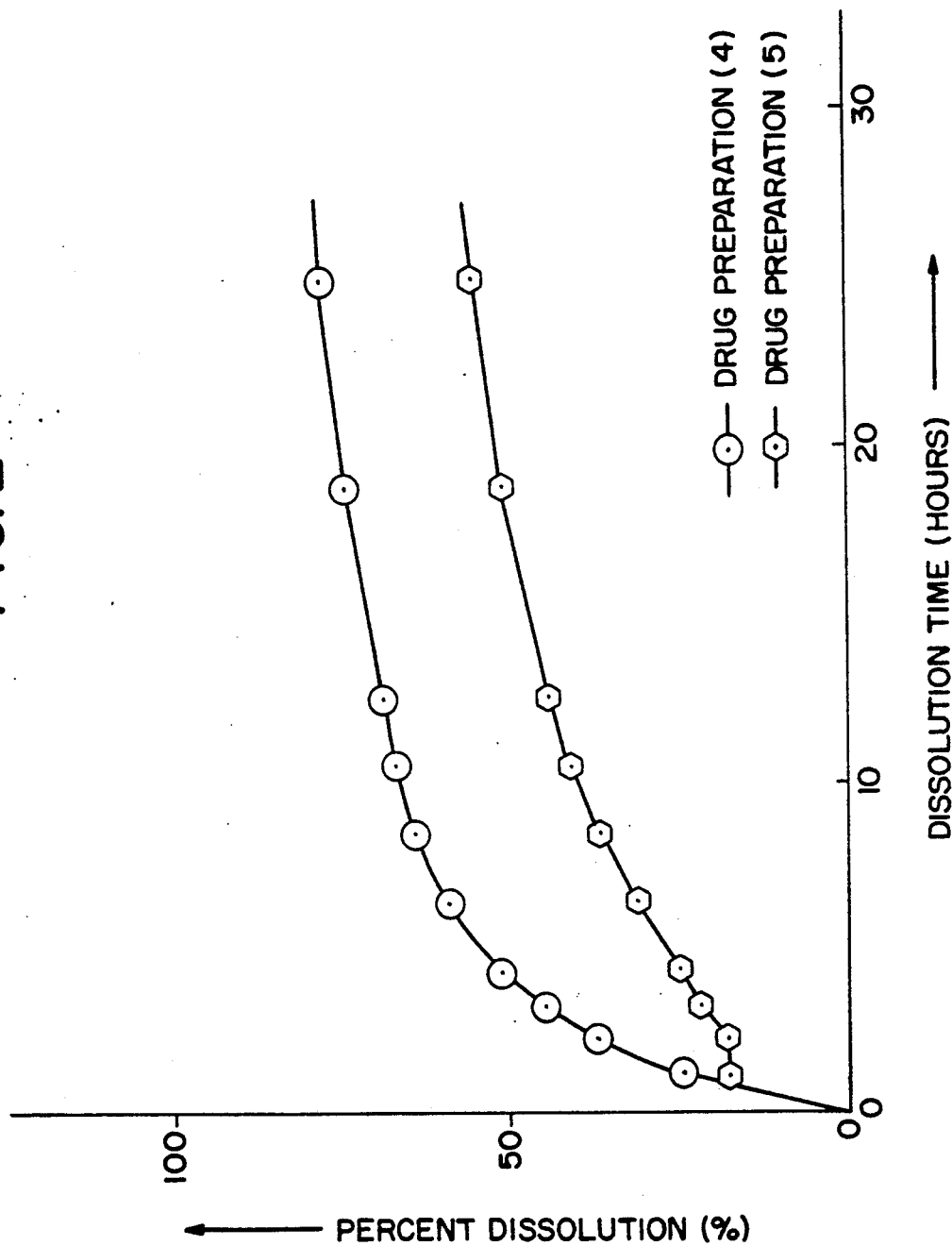

FIG. 2 illustrates a dissolution curve of the drug preparation (4) in which steric acid is incorporated as a sole lipidic substance instead of mixing the oil component among the three essential components in the present invention. Comparing the dissolution curve of the drug preparation (4) with that of the drug preparation (5) which contained all the three essential components of this invention, it is appreciated that the control of the velocity of dissolution of the drug (bunazosin hydrochloride) was considerably improved in the drug preparation (5) owing to the addition of sesame oil in the small amount of 50 g (5%).

Figure 3:
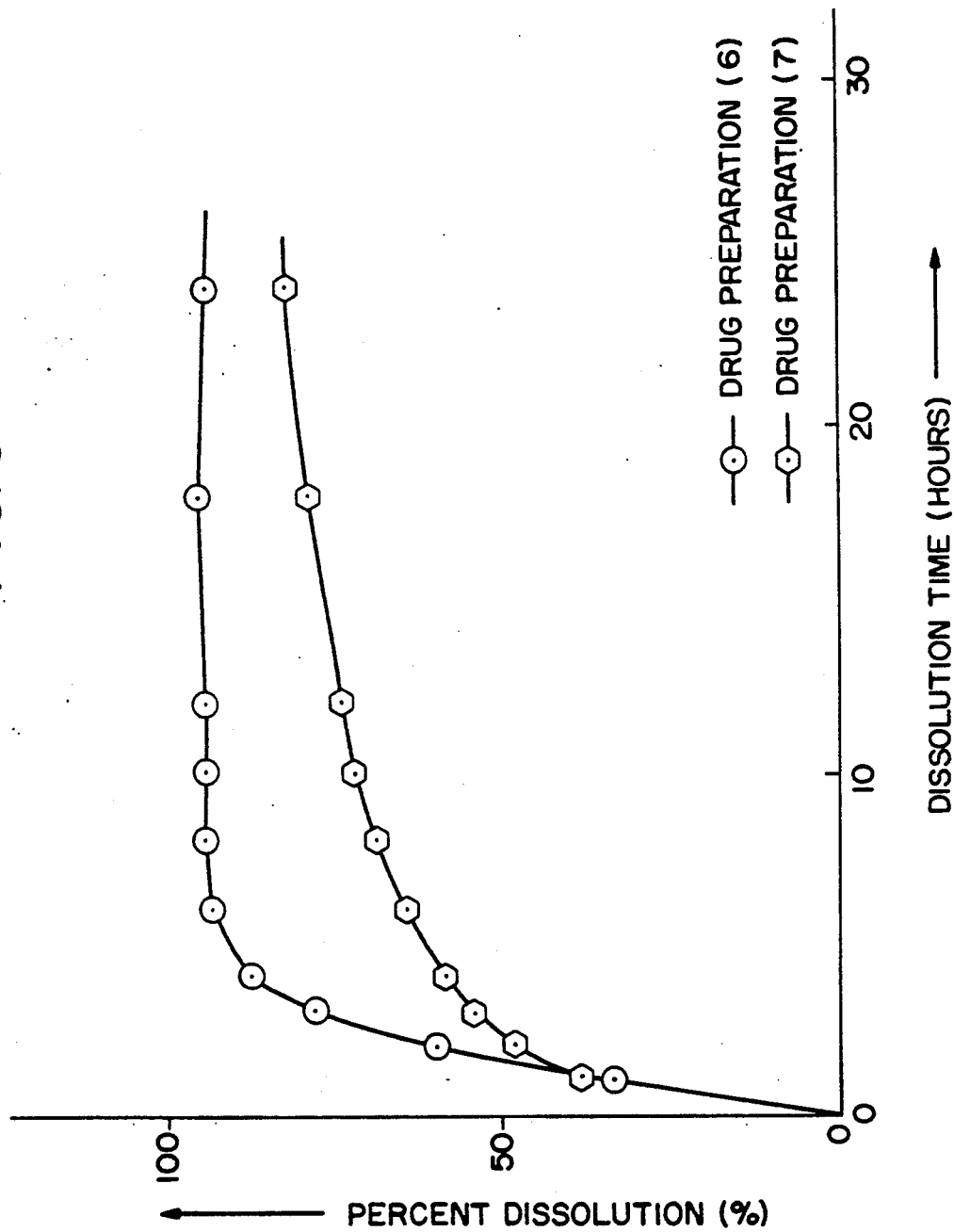

FIG. 3 depicts the velocities of dissolution of the drug, i.e., theophylline contained in the drug preparations (3) and (4) in Example 3. From the dissolution curves, it is possible to have exactly the same analytical observation and understanding as those set forth above with respect to FIG. 2.

Figure 4:
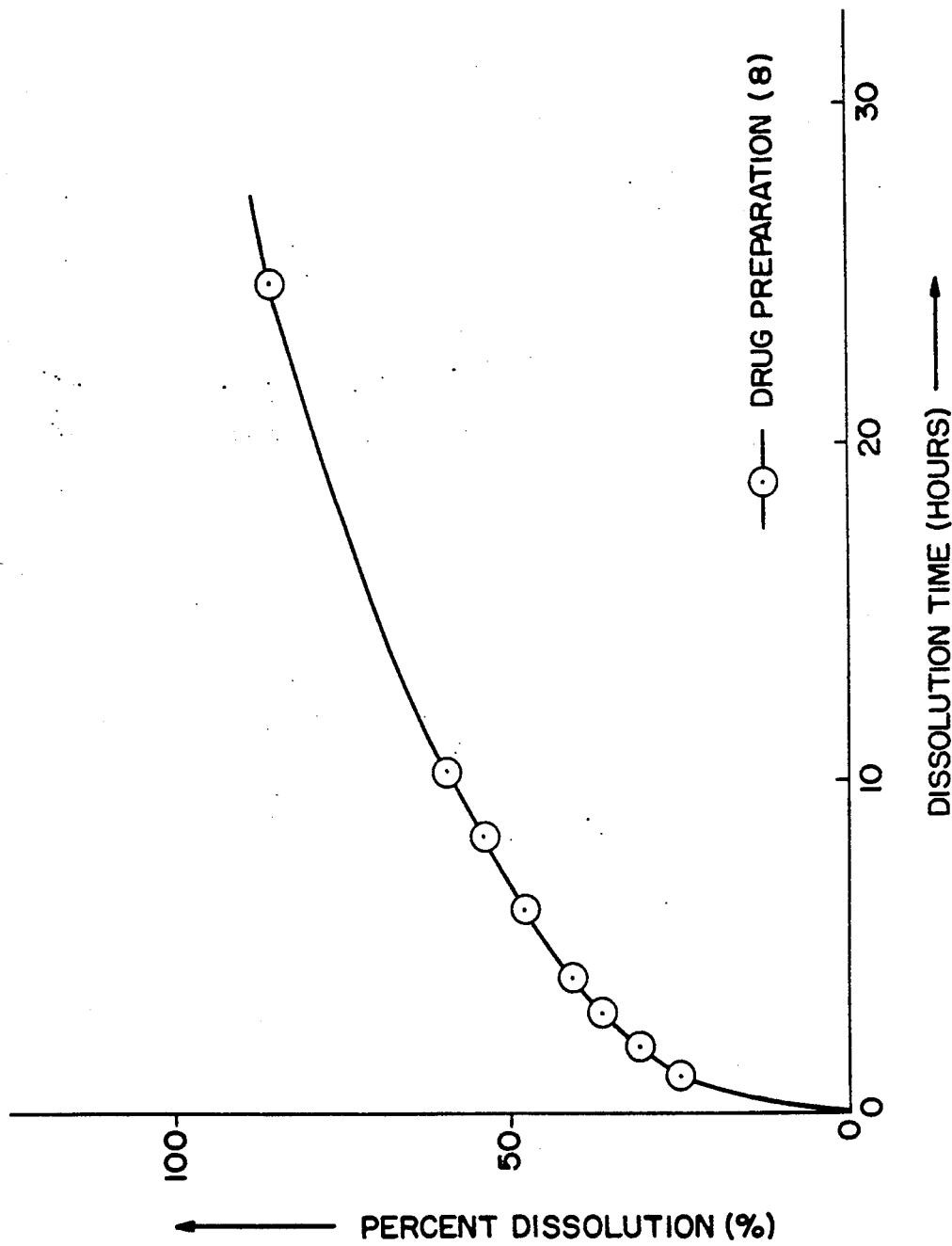
Figure 5:
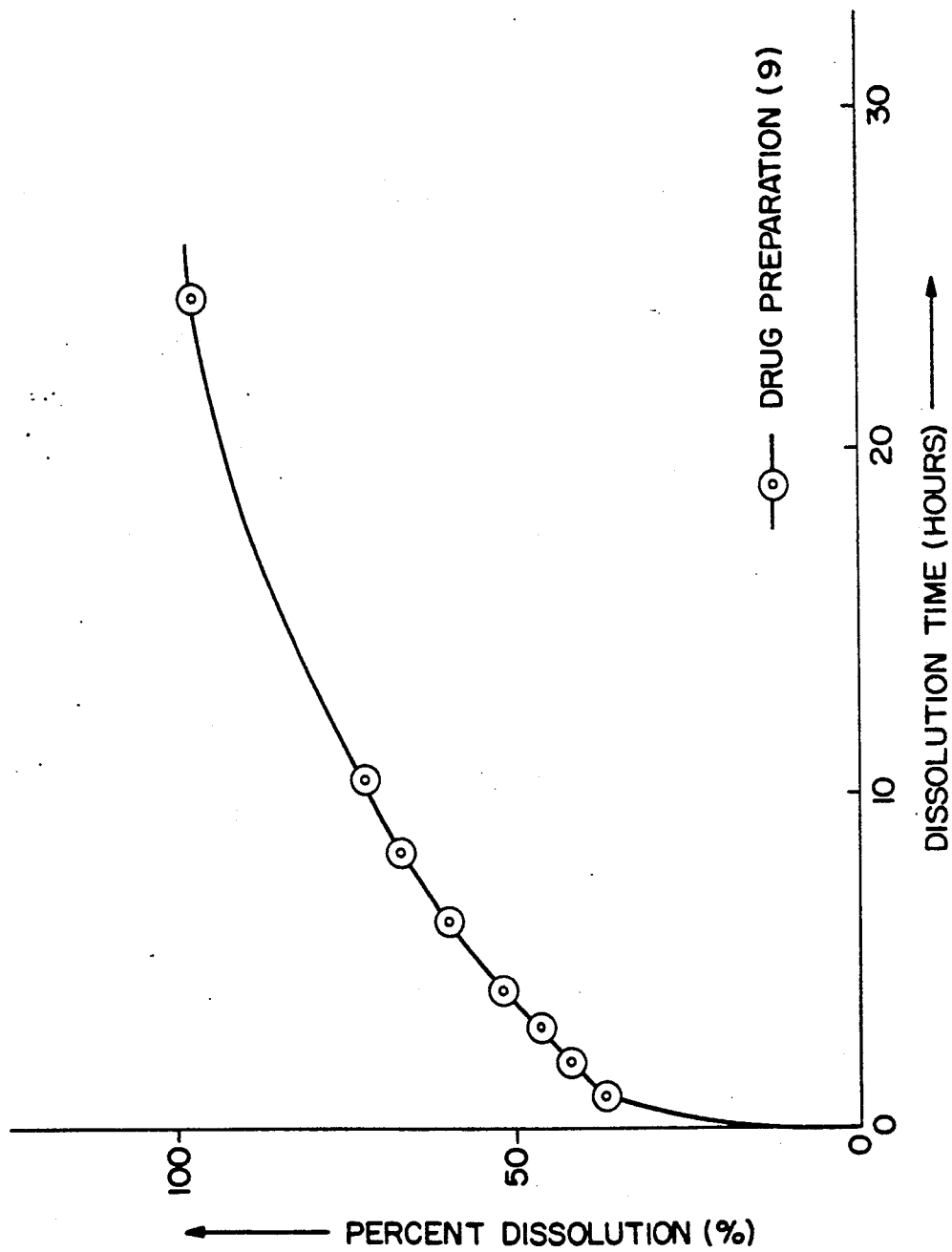

FIGS. 4 and 5 show the velocity of dissolution of the drug preparation (8) in Example 4 and that of the drug preparation (9) in Example 5. The dissolution curves of these drug preparations indicate the achievement of good dissolution control practically similar to the dissolution curves of the above drug preparations (2), (3), (5) and (7).

Having now fully described the invention, it will be apparent to one of ordinary skill in the art that many changes and modifications can be made thereto without departing from the spirit or scope of the invention as set forth herein.

We claim:

1. A sustained-release drug preparation comprising, as essential components:
   (a) a water-soluble pharmaceutical drug;
   (b) a lipid substance which is solid or semi-solid at room temperature selected from the group consisting of stearic acid, monostearate, distearate and tristearate of glycerin, hydrogenated castor oil, stearyl alcohol and sucrose esters of fatty acids; and
   (c) a vegetable oil or a synthetic oil which is liquid at said room temperature.

2. The sustained-release drug preparation as claimed in claim 1, wherein the water-soluble pharmaceutical drug is at least one drug selected from the group consisting of bunazosin hydrochloride, phenylpropanolamine, chlorpheniramine maleate and theophylline.

3. The sustained-release drug preparation as claimed in claim 1, wherein the vegetable oil is selected from the group consisting of soybean oil, cottonseed oil, sesame oil, peanut oil, olive oil, sunflower oil; and the synthetic oil is selected from the group consisting of octyldodecyl glyceride, glycerin monocaprylate, glycerin dicaprylate and silicone oil.

4. A sustained-release drug preparation comprising, as essential components, bunazosin hydrochloride, sucrose esters of fatty acids and octyldodecyl glyceride.

5. The sustained-release drug preparation according to claim 4 wherein bunazosin hydrochloride is employed at 100 parts, the sucrose ester of a fatty acid is employed at 600 parts and octyldodecyl glyceride is employed at 200 parts.

* * * * *